US010149981B2

(12) United States Patent
Stahmann et al.

(10) Patent No.: US 10,149,981 B2
(45) Date of Patent: Dec. 11, 2018

(54) AUTHENTICATION OF SHOCK THERAPY DEFERRAL

(71) Applicant: Cardiac Pacemakers, Inc., St. Paul, MN (US)

(72) Inventors: Jeffrey E. Stahmann, Ramsey, MN (US); Dan C. Goldman, North Oaks, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 15/584,987

(22) Filed: May 2, 2017

(65) Prior Publication Data

US 2017/0319865 A1 Nov. 9, 2017

Related U.S. Application Data

(60) Provisional application No. 62/331,047, filed on May 3, 2016.

(51) Int. Cl.
*A61N 1/00* (2006.01)
*A61N 1/39* (2006.01)
*A61N 1/372* (2006.01)

(52) U.S. Cl.
CPC ....... *A61N 1/3987* (2013.01); *A61N 1/37247* (2013.01); *A61N 1/37258* (2013.01); (Continued)

(58) Field of Classification Search
CPC .. A61N 1/3987; A61N 1/3993; A61N 1/3925; A61N 1/3956
See application file for complete search history.

(56) References Cited

U.S. PATENT DOCUMENTS 5,113,869 A 5/1992 Nappholz et al.
5,792,205 A 8/1998 Alt et al.
(Continued)

FOREIGN PATENT DOCUMENTS

WO 2012100219 7/2012

OTHER PUBLICATIONS

"International Search Report and Written Opinion," for PCT Application No. PCT/US2017/030880 dated Aug. 15, 2017 (12 pages).
(Continued)

*Primary Examiner* — Mallika D Fairchild
(74) *Attorney, Agent, or Firm* — Pauly, DeVries Smith & Deffner LLC

(57) ABSTRACT

The current technology relates to a shock deferral unit that is portable by an ambulatory patient. The shock deferral unit has a bi-directional communication device configured to receive a notification of an impending shock from a defibrillator and configured to send an instruction to defer the impending shock to the defibrillator. An authentication interface is configured to receive authentication data from a user. A user instruction interface is configured to receive the instruction to defer the impending shock from the user. An authentication device is configured to authenticate the user based on the authentication data and instruct the bi-directional communication device to send the instruction to defer a shock upon authentication and receipt of the instruction to defer the shock.

16 Claims, 5 Drawing Sheets

(52) U.S. Cl.
CPC ......... *A61N 1/3925* (2013.01); *A61N 1/3956* (2013.01); *A61N 1/3993* (2013.01); *A61N 1/37217* (2013.01)

(56) References Cited

U.S. PATENT DOCUMENTS

| | | | | |
|---|---|---|---|---|
| 6,681,003 | B2 | 1/2004 | Linder et al. | |
| 6,804,554 | B2 | 10/2004 | Ujhelyi et al. | |
| 6,865,424 | B2 | 3/2005 | Daum et al. | |
| 7,551,962 | B2 | 6/2009 | Daum et al. | |
| 7,734,345 | B2 | 6/2010 | Cinbis | |
| 7,974,689 | B2 | 7/2011 | Volpe et al. | |
| 8,271,082 | B2 | 9/2012 | Donnelly et al. | |
| 2004/0230246 | A1 | 11/2004 | Stein et al. | |
| 2005/0177051 | A1* | 8/2005 | Almen | A61B 5/02405 600/509 |
| 2007/0265667 | A1 | 11/2007 | Muessig et al. | |
| 2008/0021524 | A1 | 1/2008 | Goscha et al. | |
| 2009/0275805 | A1* | 11/2009 | Lane | A61B 5/01 600/300 |
| 2010/0114206 | A1 | 5/2010 | Kaemmerer et al. | |
| 2014/0031885 | A1 | 1/2014 | Elghazzawi et al. | |
| 2014/0058468 | A1 | 2/2014 | Hoyme et al. | |
| 2015/0217121 | A1 | 8/2015 | Subramanian et al. | |
| 2016/0250490 | A1* | 9/2016 | Hoffman | A61N 1/37252 607/60 |

OTHER PUBLICATIONS

"What is the LiveVest Wearable Defibrillator?" Zoll LifeVest Wearable Defibrillator by Zoll Medical Corporation URL <http://lifevest.zoll.com/medical-professionals> accessed Feb. 22, 2016 (2 pages).

* cited by examiner

AUTHENTICATION OF SHOCK THERAPY DEFERRAL

This application claims the benefit of U.S. Provisional Application No. 62/331,047, filed May 3, 2016, the contents of which are herein incorporated by reference.

FIELD OF THE TECHNOLOGY

The technology disclosed herein generally relates to shock therapy deferral. More particularly, the technology disclosed herein relates to systems and methods for authentication of shock therapy deferral.

BACKGROUND

In spite of the many advances in tachyarrhythmia discrimination in implantable and wearable defibrillators, there are still instances when delivery of shock therapy is inappropriate. Inappropriate shocks are painful and in some cases hazardous to the patient. On the other hand, failure to deliver an appropriate shock treatment is also hazardous to the patient. Allowing patients and caregivers to defer an impending shock treatment is generally desirable to avoid inappropriate shocks, but challenges include reducing the risk to the patient that human error or inadvertent interaction with the system results in inappropriate shock deferral.

SUMMARY

Some aspects of the technology disclosed herein relate to a shock deferral unit that is generally portable by an ambulatory patient. A bi-directional communication device is configured to receive a notification of an impending shock from a defibrillator and configured to send an instruction to defer the impending shock to the defibrillator. An authentication interface is configured to receive authentication data from a user. A user instruction interface is configured to receive the instruction to defer the impending shock from the user, and an authentication device is configured to authenticate the user based on the authentication data and instruct the bi-directional communication device to send the instruction to defer a shock upon authentication and receipt of the instruction to defer the shock.

According to some examples, the bi-directional communication device is a radio. In addition or alternatively, the shock deferral unit has a user interface configured to display the notification of the impending shock. In addition or alternatively, the shock deferral unit is configured to be pocketable by a patient. In addition or alternatively, the shock deferral unit is configured to be worn by patient. In addition or alternatively, the shock deferral unit is configured to be at least one in the group consisting of: wearable by, manually holdable by, and pocketable by a patient. In addition or alternatively, the authentication interface is configured to receive at least one type of authentication data from the user in the group consisting of: textual, verbal, haptic, and biometric data. In addition or alternatively, the bi-directional communication device is configured to relay one or more physiological measurements sensed by the defibrillator to the user interface. In addition or alternatively, the bi-directional communication device is configured to communicate a notification of an arrhythmia sensed by the defibrillator.

Other aspects of the present technology relate to a shock deferral system. A defibrillator is configured to sense patient physiological measures, communicate a notification of impending shock, and deliver shock therapy. A bi-directional communication device may be configured to receive a notification of impending shock from the defibrillator and configured to send an instruction to defer the impending shock to the defibrillator. An authentication interface may be configured to receive authentication data from a user. A user instruction interface may be configured to receive the instruction to defer the impending shock from the user. An authentication device may be configured to receive the authentication data from the authentication interface, and authenticate the user based on the authentication data, where the defibrillator is configured to defer shock upon authentication by the authentication device and receipt of the instruction to defer the shock, wherein the authentication interface and the user instruction interface are portable by an ambulatory patient.

According to some examples, the defibrillator comprises the authentication device. In addition or alternatively, the authentication interface is configured to receive authentication data from a user and the user instruction interface is configured to send the instruction to defer shock within a 60-second time period. In addition or alternatively, the authentication device is configured to authenticate the user each time the shock deferral unit receives a notification of impending shock from the defibrillator. In addition or alternatively, the bi-directional communication device is configured to relay one or more physiological measurements sensed by the defibrillator to a user interface.

Another aspect of the present technology relates to a method. A notification of impending shock therapy is relayed from a defibrillator to a user interface, wherein the user interface is portable by an ambulatory patient. Authentication data is received from a user through an authentication interface in response to relaying the notification. The user is authenticated with the received authentication data. An instruction is received from the user to defer the impending shock therapy through a user input device. The received instruction is sent to the defibrillator to defer the impending shock therapy upon authentication.

According to some examples, a remaining deferral time is communicated after sending the received instruction to the defibrillator to defer the impending shock therapy. In addition or alternatively, receiving authentication data from a user occurs within 60 seconds of relaying the notification of impending shock. In addition or alternatively, the authentication interface is a biometric sensor. In addition or alternatively, the authentication interface is a manual user data entry device. In addition or alternatively, the authentication interface is at least one in the group consisting of: a biometric sensor, a microphone, and a manual user data entry device. In addition or alternatively, a notification of at least one of: physiological measurements sensed by the defibrillator and shock deferral status, is relayed to the user interface. In addition or alternatively, a notification of an arrhythmia sensed by the defibrillator is relayed to the user interface. In addition or alternatively, the instruction from the user is received through at least one of: a watch, a pendant, a bracelet, eyeglasses, headphones, a mobile phone, a pen, a card, a box, and an adhesive accessory. In addition or alternatively, the instruction from the user is received through at least one of: a wearable device and a pocketable device. In addition or alternatively, the received instruction to the defibrillator is sent through radio frequency. In addition or alternatively, a training mode is entered comprising soliciting a user for authentication data absent a notification of impending shock therapy.

BRIEF DESCRIPTION OF THE DRAWINGS

The current technology may be more completely understood and appreciated in consideration of the following detailed description of various examples of the current technology in connection with the accompanying drawings.

DETAILED DESCRIPTION

Implantable and wearable defibrillators have saved many lives by providing shock therapy to patients who are experiencing heart fibrillations. However, there are instances when defibrillators deliver shock therapy inappropriately, and these issues occur with defibrillators from many different manufacturers and using many different therapy algorithms. Inappropriate shocks are painful, often feeling similar to being kicked in the chest, and can be traumatic for the patient. An inappropriate shock can also be hazardous to the patient. On the other hand, failure to deliver an appropriate shock treatment is also hazardous to the patient.

Allowing patients and trained caregivers to defer an impending shock treatment is generally desirable to avoid inappropriate shocks. If a patient is conscious and lucid enough to operate a shock deferral device, it is likely medically acceptable to defer the shock. But it is a challenge to reduce the risk of an inappropriate shock deferral that can result from human error, especially from an untrained caregiver or passer-by, or from an inadvertent interaction with the system, such as in situations where the patient collapses and an object makes contact with the system in a way that instructs the system to defer the shock. Also, receiving a warning of an impending shock is a stressful situation for a patient and for a caregiver.

Systems and methods are described herein that provide an option to defer a shock and authenticate the user who is deferring the shock, thereby reducing the risk that the shock is deferred when it should be delivered. Many of the systems and methods described authenticate the user in a manner that is relatively simple to operate in a stressful situation.

Figure 1:
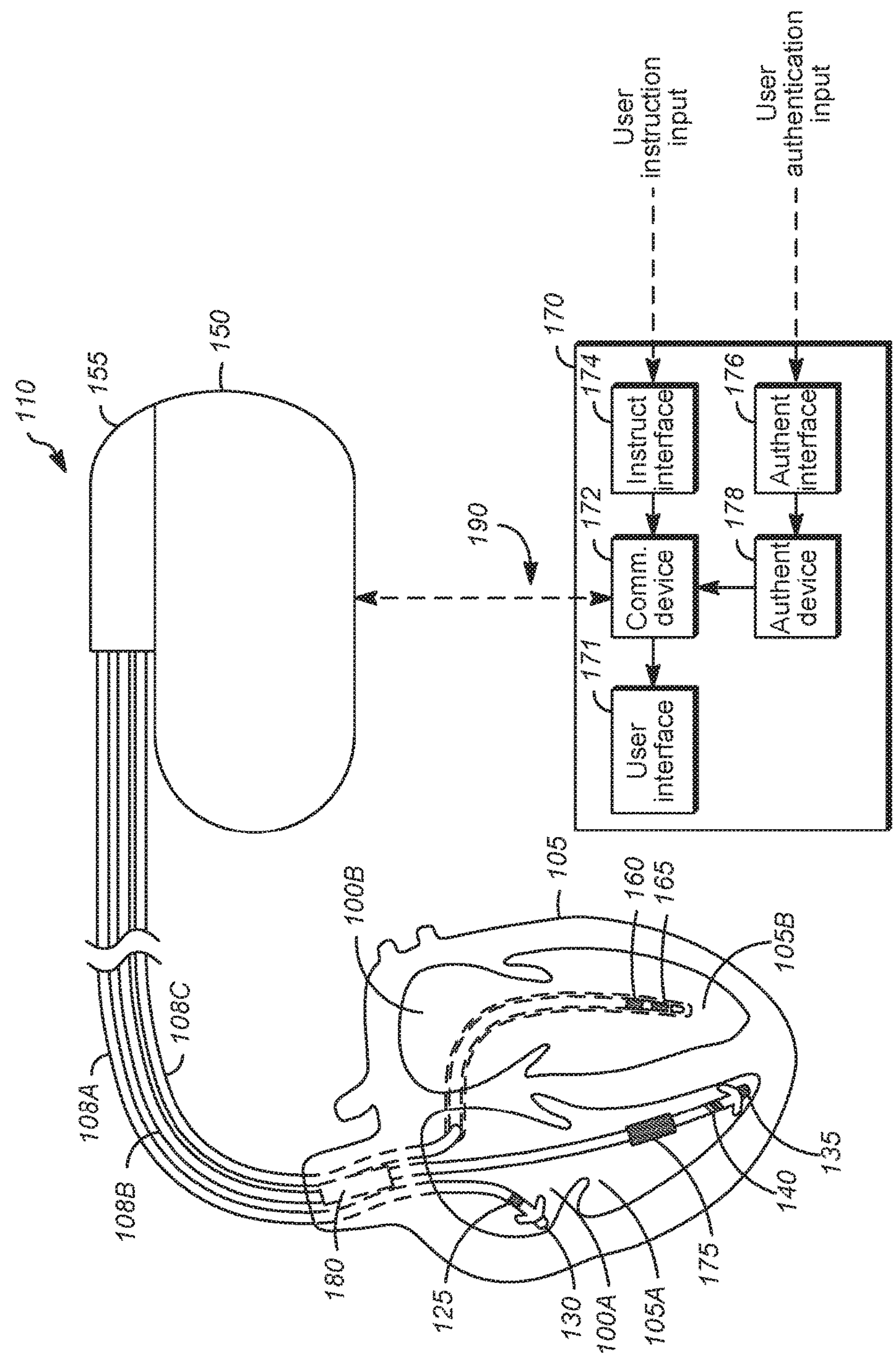
FIG. 1 depicts an example implementation of a shock deferral system consistent with the technology disclosed herein.

FIG. 1 depicts an example implementation of a system consistent with the technology disclosed herein. The system has a defibrillator 110 implanted in communication with a patient's heart 105 and a shock deferral unit 170 in bi-directional communication with the defibrillator 110. While a transvenous implantable defibrillator is described herein, it will be understood that in some embodiments the defibrillator could be a subcutaneous implantable defibrillator or a defibrillator external to the patient. For example, the defibrillators can be worn by the patient in some embodiments.

The defibrillator 110 is generally configured to sense patient physiological measures, identify when shock therapy is appropriate based on the physiological data, and deliver shock therapy when appropriate. The defibrillator 110 generally has a plurality of sensors that are configured to sense patient physiological measures. The sensors can be one or more leads 108A-C that are configured to sense an electric current and deliver an electric current to a patient's heart 105. Cardiac leads 108A-C have a proximal end that is coupled to a header 155 of the defibrillator 110 and a distal end coupled by an electrode or electrodes to one or more portions of the heart 105. The electrodes are configured to deliver defibrillation therapy, but can additionally be configured to deliver cardioversion, pacing, resynchronization therapy, or combinations thereof to at least one chamber of the heart 105. The electrodes may be electrically coupled to sense amplifiers to sense electrical cardiac signals.

By way of background, the heart 105 generally has a right atrium 100A, a left atrium 100B, a right ventricle 105A, a left ventricle 105B, and a coronary sinus extending from the right atrium 100A. The atrial lead 108A has electrodes (electrical contacts, such as ring electrode 125 and tip electrode 130) disposed in the right atrium 100A of heart 105 for sensing signals from, and/or delivering pacing therapy to, the right atrium 100A.

The ventricular lead 108B has one or more electrodes, such as tip electrode 135 and ring electrode 140, for sensing signals, delivering pacing therapy, or both sensing signals and delivering pacing therapy. The ventricular lead 108B optionally also has additional electrodes, such as for delivering atrial cardioversion, atrial defibrillation, ventricular cardioversion, ventricular defibrillation, or combinations thereof to the heart 105. Such electrodes typically have larger surface areas than pacing electrodes in order to handle the larger energies involved in defibrillation. The ventricular lead 108B optionally provides resynchronization therapy to the heart 105.

The defibrillator 110 can have a third cardiac lead 108C attached to the defibrillator 110 through the header 155. The third cardiac lead 108C can have ring electrodes 160, 165 placed in a coronary vein lying epicardially on the left ventricle (LV) 105B via the coronary vein.

The second cardiac lead 108B can have a first defibrillation coil 175 located proximal to tip and ring electrodes 135, 140 for placement in a right ventricle (RV), and a second defibrillation coil electrode 180 located proximal to the first defibrillation coil 175, tip electrode 135, and ring electrode 140 and configured for placement in the superior vena cava (SVC). In some examples, high-energy shock therapy is delivered from the first or RV coil 175 to the second or SVC coil 180. In some examples, the SVC coil 180 is electrically tied to an electrode formed on a hermetically-sealed defibrillator can 150. This improves defibrillation by delivering current from the RV coil 175 more uniformly over the ventricular myocardium. In some examples, the therapy is delivered from the RV coil 175 only to the electrode formed on the defibrillator can 150. In some examples lead 108B does not have electrode 140 and the pacing and sensing functions of electrode 140 are performed by RV coil 175.

Other forms of electrodes include meshes and patches which can be applied to portions of heart 105 or which can be implanted in other areas of the body to help "steer" electrical currents produced by defibrillator 110. The present methods and systems will work in a variety of configurations and with a variety of sensors. Sensing among different sets of electrodes often provides directional information regarding the propagation of cardiac signals and is often referred to as sensing among different vectors. For example, in a single chamber ICD, sensing from a right ventricular tip electrode 135 to a right ventricular ring electrode 140 would be a first vector, and sensing from an RV coil 175 to an electrode on the defibrillator can 150, or a header 155, would be second vector. Various electrode configurations may be used.

EGM data can be collected for at least the right ventricular channel, with electrodes implanted in or near a ventricle. For example, a ventricular channel or vector may have a tip electrode and ring electrode for the right ventricular channel or ring electrodes for the left ventricular channel. Another channel, known as the shock channel or shock vector, can be used to collect EGM data. The shock channel is sensed using electrodes that are also used to deliver high-energy shock therapy. In one example, the shock channel has an electrode placed in the right ventricle.

The electrode configuration of defibrillators 110 used in the systems and methods described herein generally allow for the collection of patient cardiac data such as electrograms (EGMs), identify an arrhythmia from the patient cardiac data and deliver high-energy shock therapy to a patient's heart upon detection of the arrhythmia. The defibrillator 110 is also configured for bi-directional, wireless communication with the shock deferral unit 170. In some embodiments the defibrillator 110 has a radio allowing bi-directional communication via radio frequency. The defibrillator 110 is generally configured to communicate a notification of an impending shock to the shock deferral unit 170. The defibrillator 110 is generally configured to receive an instruction to defer an impending shock from the shock deferral unit 170. The defibrillator 110 is generally configured to defer an impending shock upon receipt of an instruction to defer the impending shock and authentication of the user instructing the system to defer the impending shock, which will be described in more detail, below. In some embodiments the defibrillator 110 is configured to communicate one or more physiological measurements sensed by the defibrillator 110, such as communicating a notification of a sensed arrhythmia to the shock deferral unit 170.

The shock deferral unit 170 is generally configured to notify a user of an impending shock from the defibrillator 110 and send a user instruction to optionally defer the shock to the defibrillator 110. The user may be, for example, the defibrillator patient, someone typically residing with the patient (e.g. the patient's spouse), a physician, a nurse, someone with minimal training caring for the patient (e.g. a nursing home attendant or personal care attendant) or a Good Samaritan encountering the patient at a critical time.

The shock deferral unit 170 can have a variety of configurations and implementations, but is generally portable by an ambulatory patient. Such a configuration can be desirable to enable the patient being in close proximity to the shock deferral unit 170 a majority of the time. The term "portable" means capable of being carried or moved by an ambulatory patient. In some embodiments the shock deferral unit 170 has no single outer dimension larger than 15 centimeters. In addition or alternatively, the shock deferral unit 170 has a weight of 3 kilograms or less. In addition or alternatively, the shock deferral unit has no single outer dimension larger than 5 centimeters. In addition or alternatively, the shock deferral unit 170 has a weight of 1 kilogram or less. In some embodiments the shock deferral unit is configured to be wearable by a patient. As used herein, the term "wearable" means capable of being attached to a body part of a patient or to a patient's clothing without interfering with walking. In addition or alternatively, the shock deferral unit is configured to be pocketable by the patient. In addition or alternatively, the shock deferral unit is configured to be holdable by the patient. The particular optional configurations of the shock deferral unit will be described in more detail with reference to FIGS. 3-4.

Returning to FIG. 1, the shock deferral unit 170 generally has a bi-directional communication device 172, a user interface 171, a user instruction interface 174, an authentication interface 176, and an authentication device 178. While the shock deferral unit 170 is depicted as a single component, in multiple embodiments the shock deferral unit 170 can be multiple components. In various embodiments each of the bi-directional communication device 172, the user interface 171, the user instruction interface 174, the authentication interface 176 and the authentication device 178 are configured to be portable by an ambulatory patient.

The bi-directional communication device 172 is generally configured for bi-directional communication with the defibrillator 110, generally through wireless signals 190 with the defibrillator 110. The bi-directional communication device 172 can have a radio. The wireless signals 190 can be radio frequency (RF), inductive, conductive or other telemetry signals. The bi-directional communication device 172 is generally configured to receive a notification of impending shock from a defibrillator 110 and also configured to send an instruction to defer the shock to the defibrillator 110, where the instruction was received from a user.

The bi-directional communication device 172 can also be configured to relay one or more physiological measurements sensed by the defibrillator 110. For example, the bi-directional communication device 172 can be configured to communicate a notification of an arrhythmia sensed by the defibrillator, in a variety of embodiments. In another example, the bi-directional communication device 172 can be configured to communicate physiological measures such as heart rate, blood pressure, respiration rate, activity level, and combinations thereof.

In some embodiments, the bi-directional communication device 172 communicates with the defibrillator 110 at scheduled intervals to download patient physiological data from the defibrillator. For example, the bi-directional communication device 172 can download patient physiological data from the defibrillator every 10 minutes, 5 minutes, 1 minute, or less. In some embodiments, the bi-directional communication device 172 communicates in real time with the defibrillator 110. In various embodiments, the defibrillator 110 and the bi-directional communication device 172 communicate in real time at least in the event of an impending shock.

The bi-directional communication device 172 can send data from the defibrillator 110 to the user interface 171 for display on the user interface 171, in a variety of embodiments. The user interface is generally configured to provide output data to a user. In a variety of embodiments the user interface 171 is a display screen, but the user interface 171 can also incorporate speakers, haptic, or other outputs to communicate data to a user. In a variety of embodiments the user interface 171 is configured to display the notification of impending shock received by the bi-directional communication device 172. In some embodiments, the user interface 171 is configured to display one or more physiological measurements, such as a notification of arrhythmia, sensed by the defibrillator 110 and relayed by the bi-directional communication device 172. Upon deferring an impending shock therapy, the user interface 171 is configured to communicate the deferral time remaining before the next impending shock therapy.

While in the current embodiment the user interface 171 is depicted as a component of the shock deferral unit 170, in some embodiments the user interface 171 is a separate device from the shock deferral unit 170. In such embodiments the shock deferral unit 170 and the user interface 171 are each configured to be portable by an ambulatory patient. For example, the user interface 171 can be a smart-phone that is in communication with the shock deferral unit 170.

The user instruction interface 174 of the shock deferral unit 170 is generally configured to receive an instruction to defer an impending shock from a user. In some embodiments the user instruction interface 174 can be configured to receive various types of user data as an instruction to defer an impending shock. For example, the user instruction interface 174 can be a manual data entry device such as a physical or virtual button. In other examples, the user instruction interface 174 is a microphone configured to receive a user's verbal instruction to defer shock. The verbal instructions to defer shock can be spoken phrases from a patient such as "don't shock me" or "defer shock."

In a variety of embodiments, when the user interface 171 notifies the user of the impending shock from the defibrillator 110, the user interface 171 also prompts the user for an instruction to defer the impending shock. While in the current embodiment the user instruction interface 174 is depicted as a component of the shock deferral unit 170, in some embodiments the user instruction interface 174 is a separate device from the shock deferral unit 170. In such embodiments the shock deferral unit 170 and the user instruction interface 174 are each configured to be portable by an ambulatory patient. In some embodiments the user instruction interface 174 and the user interface 171 can be incorporated in a single component, such as a smartphone, that is separate from the shock deferral unit 170.

The authentication interface 176 of the shock deferral unit 170 is generally configured to receive authentication data from the user who enters the instruction to defer the shock therapy. The authentication device 178 is generally configured to receive the authentication data from the authentication interface 176 and authenticate the user based on the user authentication data. Upon authentication, in various embodiments, the authentication device 178 instructs the bi-directional communication device to send the instruction to defer a shock upon receipt of the instruction to defer the shock. The authentication interface 176 and the authentication device 178 are generally configured to authenticate the user each time the shock deferral unit 170 receives a notification of impending shock from the defibrillator 110.

The authentication interface 176 is generally configured to be portable by an ambulatory patient. The authentication interface 176 can be configured to receive various types of user data to authenticate the identity of the user. For example, the authentication interface 176 can be a biometric sensor configured to receive biometric data to authenticate the identity of the user. As another example, the authentication interface 176 can be an input configured to receive coded data from the user, such as a manual user data entry device such as a keypad, a keyboard, buttons, or a touch screen, as examples. In general the authentication interface 176 authenticates the user upon an affirmative act by the user to authenticate himself/herself. If the user is the patient within whom the defibrillator is implanted, the patient's affirmative act of entering authentication data can be an indicator that the patient is hemodynamically stable and is, therefore, sufficiently conscious and lucid to defer the impending shock therapy. If the user is a caregiver such as a family member, authentication of the user is an indicator that the caregiver has been properly trained to defer an impending shock. Authentication of the user is generally accomplished in real time relative to notification of impending shock and receipt of the instruction to defer shock. In this way, authentication can ensure that the instruction to defer shock was an affirmative act by the user rather than the result of an accidental or malicious act.

Biometric data used to authenticate the identity of a user can be electrical, visual, mechanical, acoustic, and/or chemical biometric data. Some examples of electrical biometric data that can be collected by the authentication interface 176 for user authentication are user EKG, EEG, EOG, and EMG data. In such embodiments the authentication interface 176 can have one or more electrodes. Another example of electrical biometric data that can be collected for user authentication is the impedance at least partially through the body of the user. In such embodiments the authentication interface 176 can have two electrodes: a first electrode configured to make contact with a patient's body at a first location and a second electrode configured to make contact with the patient's body at a second location to define an electrical pathway from the first location to the second location. Some examples of visual biometric data that can be collected for user authentication by the authentication interface 176 are images of the user's iris, face, hand, ear, skin, and fingerprint. In such embodiments the authentication interface 176 can have a camera, scanner, or other visual sensor such as a fingerprint sensor.

Some examples of mechanical biometric data that can be collected for user authentication by the authentication interface 176 are the user's heartbeat, blood flow, respiration and airflow. In such embodiments the authentication interface 176 can have a mechanical sensor to collect such user data. Some examples of acoustical biometric data that can be collected by the authentication interface 176 are the user's heart, respiration, and voice. In such embodiments the authentication interface 176 can have a microphone to collect such user data. Some examples of chemical biometric data that can be collected for user authentication by the authentication interface 176 are DNA, breath, tissue, saliva, blood, sweat, and tears. In such embodiments the authentication interface 176 can have a chemical sensor or an electrochemical sensor to collect such user data.

Coded data used to authenticate the identity of the user can be textual, verbal, and/or haptic data entered by the user. Some examples of textual data that can be collected by the authentication interface 176 for user authentication are a textual password and a textual response to a query. In such embodiments the authentication interface 176 can have a keyboard, keypad, or touchscreen. Some examples of verbal data that can be collected by the authentication interface 176 for user authentication are a verbal password and a verbal response to a query. In such embodiments the authentications interface 176 can have a microphone. Some examples of haptic data that can be collected by the authentication interface 176 for user authentication are a touch pattern and touch sequence. In such embodiments the authentication interface 176 can have a touch screen or touch pad.

In some embodiments the authentication interface 176 and the user instruction interface 174 is the same component or combinations of components. In some embodiments the authentication interface 176, the user instruction interface 174, and the user interface 171 are a single cohesive component or combinations of components. For example, the authentication interface 176, the user instruction interface 174 and the user interface 171 can be defined by a keypad and corresponding screen. In the authentication interface 176, the user instruction interface 174 and the user interface 171 can be defined by a touchscreen.

The authentication device 178 is configured to authenticate a user based on the authentication data received from the user through the authentication interface 176. In some embodiments, the authentication device 178 is configured to instruct the bi-directional communication device to send an instruction to defer a shock upon authentication of the user and upon receipt of the instruction to defer the shock. In a variety of embodiments the authentication device 178 can be in communication with a memory or other data source that has comparison data. The comparison data can be matched to the authentication data input by the user to authenticate the user. In one embodiment, the comparison data is EKG data sensed by the defibrillator. In another embodiment, the comparison data is a passcode or a touch-screen pattern stored in memory.

In embodiments where the user instruction interface 174, the authentication interface 176 and the user interface 171 are combined into a single component separate from the bi-directional communication device 172, all or part of the authentication device 178 can be incorporated into either component. In some embodiments the user instruction interface 174, the authentication interface 176, the authentication device 178, and the user interface 171 can be incorporated into the functionality of a smart phone or a watch (as examples) and the bi-directional communication device 172 can be an intermediary component that relays communication between the defibrillator 110 and the smart phone. Other implementations will be described below with reference to FIGS. 3-4.

Although the embodiment in FIG. 1 shows the authentication device 178 separate from the defibrillator 110, in some embodiments all or part of the authentication device 178 resides in the defibrillator 110. In such embodiments the defibrillator 110 is configured to defer shock upon receipt of the instruction to defer shock and user authentication. For example, the authentication device 178 can be configured to receive the instruction to defer shock from the bi-directional communication device 172 and cause the defibrillator to defer shock upon authentication of the user.

Figure 2:
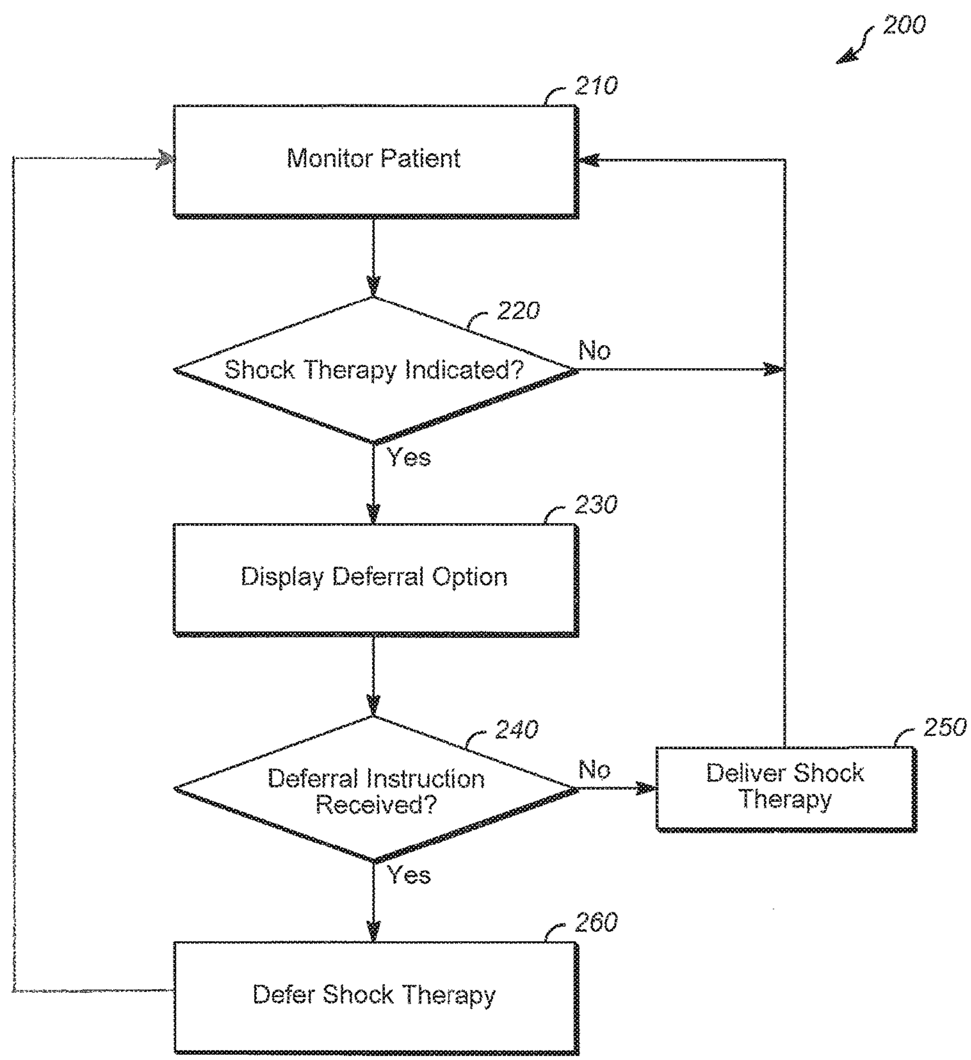
FIG. 2 is a flow chart consistent with some examples of the technology disclosed herein.

FIG. 2 is a flow chart consistent with some embodiments of the technology disclosed herein. The system generally monitors the patient 210. If shock therapy is indicated 220, the system displays a deferral option 230 on the user interface. If shock therapy is not indicated 220, the system continues to monitor the patient 210. Upon display of the deferral option 230, the system delivers shock therapy 250 if a deferral instruction is not received 240 and defers shock therapy 260 is the deferral instruction is received 240. Upon deferral of shock therapy 260, the system monitors the patient 210 and if shock therapy is still indicated 220 and if the system receives a second deferral instruction before timeout 240, then the next impending shock is deferred. If the system does not receive a second deferral instruction before timeout 240, then the next impending shock is delivered 250.

The defibrillator generally determines whether shock therapy is indicated 220 through analysis of the patient physiological measures collected by the defibrillator. When shock therapy is indicated 220, the shock deferral unit relays a notification of the impending shock therapy from the defibrillator to the user interface. The notification can be a visual and/or audio notification. The user interface will generally display the deferral option 230 to the user, which provides the user the option of deferring the shock therapy if it is appropriate. Generally the user interface will provide the option to defer shock to the user within a relatively short time period following the notification of impending shock therapy, after which the defibrillator will deliver the shock treatment. In some embodiments the user interface displays the deferral option to the user for 90 seconds following the notification of impending shock therapy. In some embodiments the user interface displays the deferral option to the user for 60 seconds following the notification of impending shock therapy. In some embodiments the user interface displays the deferral option to the user for 15 seconds following the notification of impending shock therapy. In a number of embodiments the user interface displays the amount of time the user has to defer the impending shock therapy.

A deferral instruction is received 240 from the user when the shock deferral unit receives an instruction from the user to defer the impending shock through a user input device. In a variety of embodiments, the deferral instruction is received 240 by the defibrillator only after also receiving authentication data from the user through an authentication interface and authenticating the user with the received authentication data. As such, in some embodiments the system receives authentication data from the user within 90 seconds, 60 seconds, or 15 seconds of relaying the notification of impending shock from the defibrillator to receive the deferral instruction 240.

In some embodiments entering the instruction to defer shock and entering the authentication data by the user is the result of a single input by the user. For example, where the user instruction interface is a button touched or pressed by the user, the authentication interface can be a fingerprint sensor to authenticate the user via fingerprint, such that the act of instructing the system to defer shock therapy also authenticates the user. In addition or alternatively, where the user instruction interface is a button touched or pressed by the user, the authentication interface can have an impedance sensor and define a bridge for an electrical pathway through the patient's body. The impedance sensor can measure the impedance through the electrical pathway to authenticate the user such that the act of instructing the system to defer shock therapy also provides verification that the individual wearing the user instruction interface is the same individual who is touching the button. As another example, where the user instruction interface is a microphone configured to receive a user's verbal instruction to defer shock, the authentication interface can authenticate the user based on the user's voice. In some embodiments entering the instruction to defer shock and entering the authentication data by the user is the result of multiple inputs by the user, such as touching/pressing a button to instruct the system to defer shock and entering a passcode for authentication.

Upon receiving the instruction to defer shock and authenticating the user, the shock deferral unit sends the received instruction to defer shock to the defibrillator. The received instruction can be sent to the defibrillator through radio frequency wireless signals, for example. Upon deferral of the shock therapy 260, the system defers the shock for a predetermined period of time following receiving the instruction to defer the impending shock if shock therapy is still indicated 220. The predetermined period of time is referred to herein as the "deferral time." The deferral time can be less than or equal to 60 seconds, less than or equal to 45 seconds, or less than or equal to 15 seconds. Within the deferral time, the patient is again monitored 210 and if shock therapy is still indicated 220 the deferral option is displayed 230 again and the user instruction interface can be configured to receive a second user instruction to again defer the impending shock.

After sending the received instruction to the defibrillator to defer the impending shock therapy, the system can be configured to communicate the remaining deferral time to the user. Upon expiration of the deferral time, if no second user instruction to defer shock has been received 240, and if shock therapy is still indicated 220 by patient physiological measures, the defibrillator delivers the shock therapy 250. If a second deferral instruction is received 240 within the deferral time, shock therapy is deferred 260 a second time and the patient is monitored 210 to determine whether shock therapy is indicated 220, and the process is repeated. In some examples there can be a limit on the number of deferrals or the aggregate deferral time for individual cardiac events. In other examples there is no limit to the number of deferrals or the aggregate deferral time.

Figure 3:
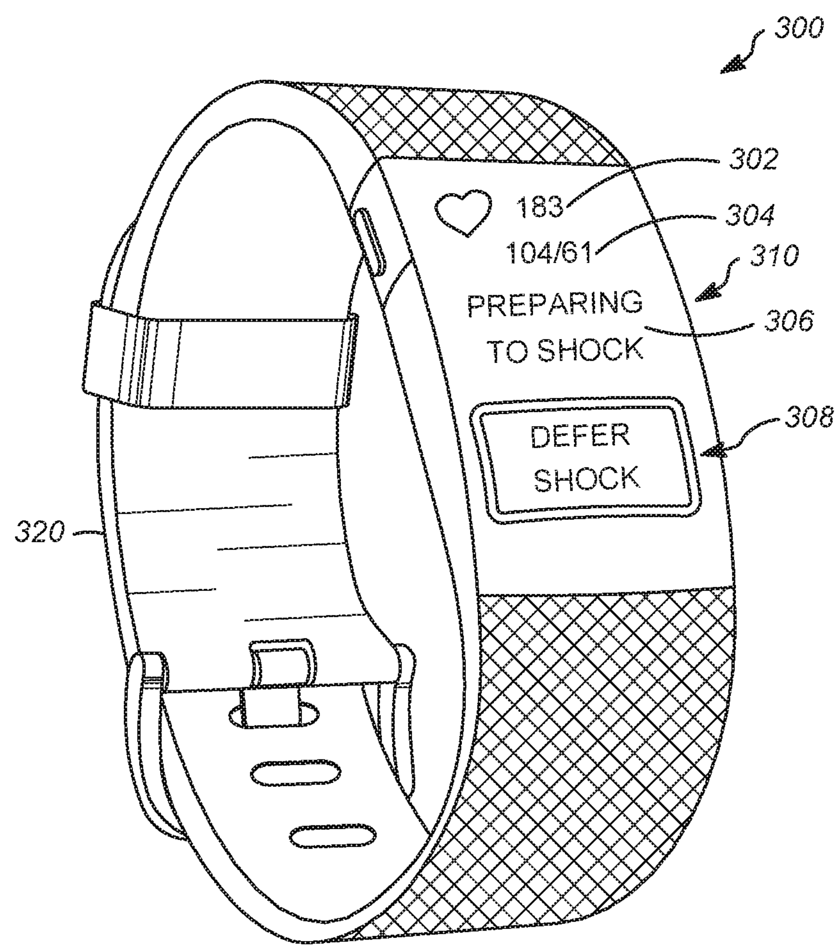
FIG. 3 is an example implementation of a shock deferral unit consistent with the technology disclosed herein.

FIG. 3 is an example implementation of a shock deferral unit 300 consistent with the technology disclosed herein. The shock deferral unit 300 is configured to be in bi-directional communication with an implantable or wearable defibrillator (see, for example, FIG. 1) to receive notification of impending shock from the defibrillator and to send an instruction to the defibrillator to defer an impending shock. The shock deferral unit 300 relays the notification of impending shock from the defibrillator to the user interface 310. The shock deferral unit 300 can have a bi-directional communication device that enables such functionality.

In the embodiment of FIG. 3, the shock deferral unit 300 is wearable by a user. In particular, the shock deferral unit 300 has a wrist strap 320 that is configured to receive the wrist of a user. The user can be a patient having an implantable or wearable defibrillator. The user interface 310 is configured to display information to the user. The user interface 310 is configured to display the notification of impending shock 306. The user interface 310 is configured to display one or more patient physiological measurements, such as user heart rate 302 and blood pressure 304. The physiological measurements can be collected by the shock deferral unit 300 itself or the physiological measurements can be those sensed by the defibrillator and relayed to the shock deferral unit 300. The user interface 310 is configured to display the option to defer shock 308 to the user.

In the embodiment of FIG. 3, the user interface 310 is also a user instruction interface configured to receive the instruction to defer shock from the user. The user interface 310 can be a touch-screen, where a user contacts or presses the "defer shock" display area 308 on the user interface 310 to select it. In embodiments, the user interface 310 is also an authentication interface configured to receive authentication data from the user. For example, the user interface 310 can incorporate a fingerprint sensor to collect user fingerprint data when the "defer shock" display area 308 option is selected. In addition or alternatively, the user interface 310 can incorporate an impedance sensor configured to take an impedance measurement through the patient's body upon contact with the "defer shock" button 308 on the user interface 310. In such an embodiment, the shock deferral unit 300 serves as a bridge of an electrical pathway through the user's body. For example, a first electrode can be disposed on the inside surface of the wrist strap 320 to make contact with the patient's wrist, and a second electrode can be defined by the "defer shock" button 308 such that when a patient wears the wrist strap 320 and selects the "defer shock" button 308 an electrical pathway through the patient's body is created. The impedance of the electrical pathway can be measured by an impedance sensor for authentication of the user. In some embodiments the user instruction interface and/or the authentication interface can be a physical button adjacent to the "defer shock" option 308 displayed on the user interface 310.

Although not visible in the current figure, the shock deferral unit 300 generally has an authentication device that is configured to authenticate the user based on the user authentication data. The authentication device can be in communication with memory having comparison data. The authentication device can be configured to compare the comparison data with the authentication data and authenticate the user when the comparison data and the authentication data matches. Upon authentication, the authentication device is configured to allow a received instruction to defer shock to be sent to the defibrillator.

While in the embodiment of FIG. 3 the shock deferral unit 300 has a similar configuration to a wrist watch, alternate configurations and additional features are certainly possible. Generally the shock deferral unit is portable by an ambulatory patient. The shock deferral unit can be configured to be worn by a patient, pocketable by a patient, and/or grasped by a patient's hands. The shock deferral unit being wearable by a patient can encompass embodiments where the shock deferral unit is adherable to the patient, such as adherable to the patient's skin. In such embodiments the electronic components of the shock deferral unit can be re-used, but the adhesive portion can be replaced. In alternate embodiments the shock deferral unit can be at least one of: a watch, a pendant, a bracelet, eyeglasses, headphones, a mobile phone, a pen, a card similar in size to a credit card, a box, and an adhesive accessory.

Figure 4:
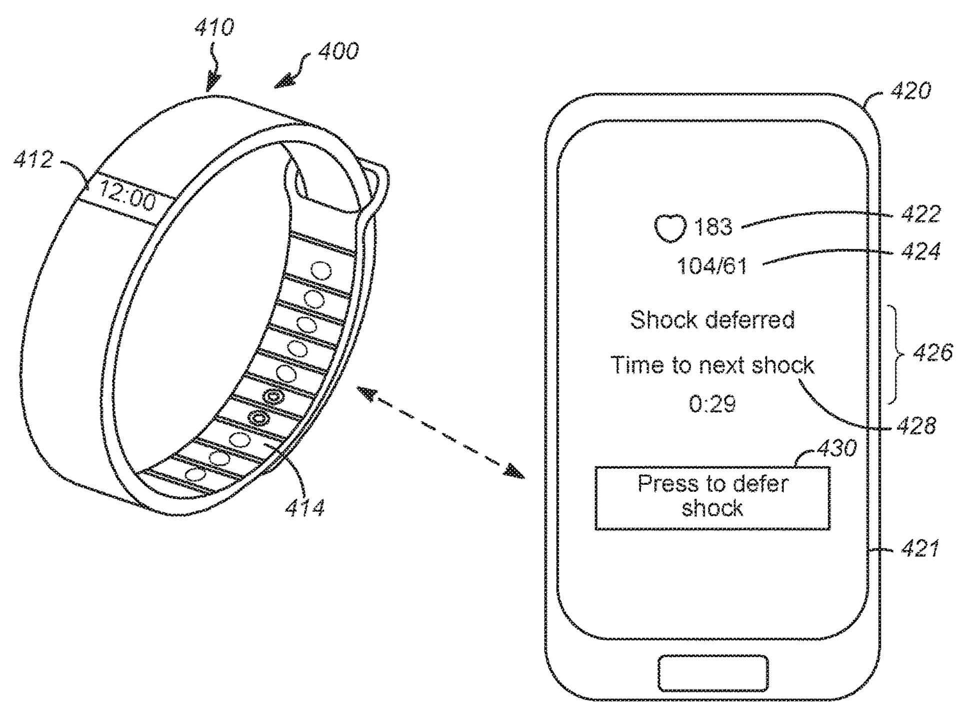
FIG. 4 depicts another example implementation of a shock deferral unit consistent with the technology disclosed herein.

FIG. 4 depicts another example implementation of a shock deferral unit 400 consistent with the technology disclosed herein. The shock deferral unit has multiple components, in the current embodiment: a defibrillator interface unit 410 and a user interface device 420 that are in bi-directional wireless communication. The defibrillator interface unit 410 and the user interface device 420 can be in bi-directional wireless communication via Bluetooth or radio communication, as examples. The user interface device 420 can be a smart phone. The defibrillator interface unit 410 has a bi-directional communicator (not visible) that is configured to be in bi-directional wireless communication with an implantable or wearable defibrillator (see, for example, FIG. 1) to receive notification of impending shock from the defibrillator and to send an instruction to the defibrillator to defer an impending shock. The defibrillator interface unit 410 relays the notification of impending shock from the defibrillator to the user interface 421.

In the current embodiment the defibrillator interface unit 410 is wearable by a user. In particular, the defibrillator interface unit 410 has a wrist strap 414 that is configured to receive the wrist of a user. The user can be a patient having an implantable or wearable defibrillator. The defibrillator interface unit 410 has an optional viewing window 412 that can display the time or other data to the user.

The user interface device 420 has a touch screen user interface 421 that is configured to display information to the user. The user interface 421 is configured to display the shock deferral status 426, which includes the remaining deferral time 428 after instructing the defibrillator to defer an impending shock. The user interface 421 is configured to display one or more patient physiological measurements, such as user heart rate 422 and blood pressure 424. Such physiological measurements can be collected by the defibrillator interface unit 410 itself or the physiological measurements can be those sensed by the defibrillator and relayed to the user interface device 420 from the defibrillator interface unit 410. The user interface 421 is configured to display the option to defer shock 430 to the user.

Similar to the embodiment described with respect to FIG. 3, the user interface 421 can also be a user instruction interface configured to receive the instruction to defer shock from the user and/or an authentication interface configured to receive authentication data from the user. Although not visible in the current figure, either the defibrillator interface unit 410 or the interface device 420 has an authentication device that is configured to authenticate the user based on the received user authentication data, as described above. Upon authentication, the authentication device is configured to allow a received instruction to defer shock to be sent to the defibrillator.

FIG. 3 depicts an example user interface after notification of impending shock therapy and FIG. 4 depicts an example user interface after the impending shock therapy had been deferred. Prior to the shock deferral unit notifying a user of an impending shock, the user interface will not provide an option to defer a shock and instead can provide other data such as respiration rate, activity level, and time and date, as examples. Following delivery of shock therapy by the defibrillator, the user interface can display a notification that the shock therapy was delivered and provide additional patient physiological data not limited to heart rate, blood pressure, and respiration rate, as examples.

In some embodiments it can be desirable for the shock deferral unit to be used in the training of patients and caregivers. As such, shock deferral units consistent with the technology disclosed herein can operate in a training mode in which the trainee is solicited for authentication data and/or a shock deferral instruction absent a notification of impending shock therapy from the defibrillator. Patients and caregivers can practice entering in authentication data.

Figure 5:
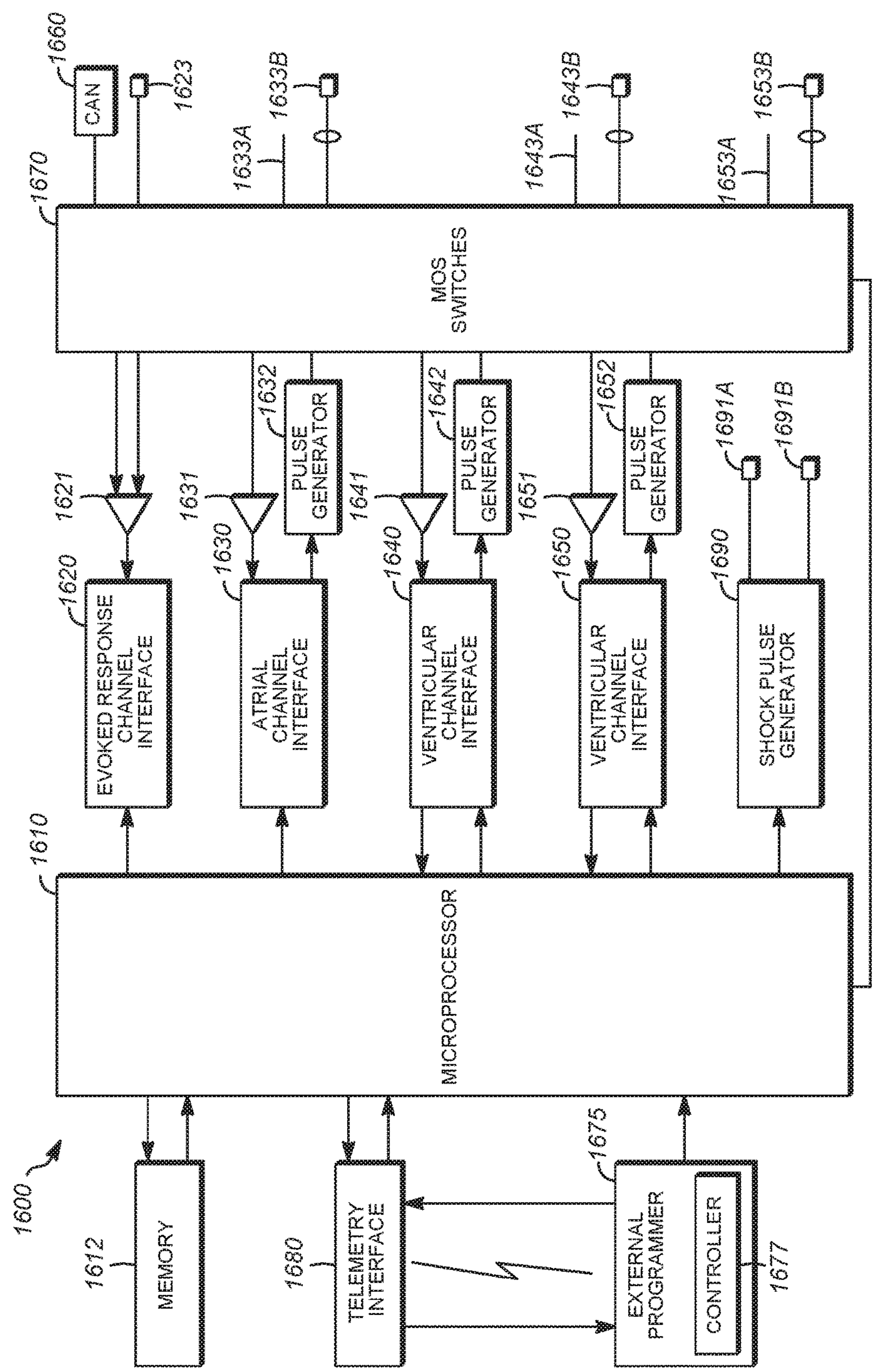
FIG. 5 is a schematic diagram of components of a defibrillator according to some embodiments.

Referring now to FIG. 5, some components of an exemplary defibrillator 1600 are schematically illustrated. The defibrillator 1600 can have a controller made up of a microprocessor 1610 communicating with a memory 1612, where the memory 1612 can have a ROM (read-only memory) for program storage and a RAM (random-access memory) for data storage. The controller can be implemented by other types of logic circuitry (e.g., discrete components or programmable logic arrays) using a state machine type of design, but a microprocessor-based system is preferable. The controller is capable of operating the defibrillator 1600 in a number of programmed modes where a programmed mode defines how pulses are output in response to sensed events and expiration of time intervals.

A telemetry link 1680 is provided for communicating with an external programmer 1675 and shock deferral device (see, for example, elements 170 of FIG. 1, 300 of FIGS. 3 and 400 in FIG. 4). In one example the same telemetry mode (e.g. RF) is used between defibrillator 1600 and external programmer 1675 and shock deferral device. In another example a different telemetry mode is used between defibrillator 1600 and external programmer 1675 (e.g. inductive) and shock deferral device (e.g. RF). The external programmer is a computerized device with a controller 1677 that can interrogate the defibrillator 1600 and receive stored data as well as adjust the operating parameters of the pacemaker.

The defibrillator 1600 has an atrial sensing/pacing channel comprising ring electrode 1633A tip electrode 1633B sense amplifier 1631, pulse generator 1632, and an atrial channel interface 1630 which communicates bi-directionally with a port of microprocessor 1610. The device also has two ventricular sensing/pacing channels that similarly include ring electrodes 1643A and 1653A tip electrodes 1643B and 1653B sense amplifiers 1641 and 1651, pulse generators 1642 and 1652, and ventricular channel interfaces 1640 and 1650. For each channel, the electrodes are connected to the defibrillator 1600 by a lead and used for both sensing and pacing. A MOS switching network 1670 controlled by the microprocessor is used to switch the electrodes from the input of a sense amplifier to the output of a pulse generator. A shock channel is also provided comprising a shock pulse generator 1690 and shock electrodes 1691A and 1691B that enables the device to deliver a defibrillation shock to the heart when fibrillation or other tachyarrhythmia is detected. The defibrillator 1600 also has an evoked response sensing channel that comprises an evoked response channel interface 1620 and a sense amplifier 1621 that has its differential inputs connected to a unipolar electrode 1623 and to the device housing or can 1660 through the switching network 1670. The evoked response sensing channel may be used to verify that a pacing pulse has achieved capture of the heart in a conventional manner or, as explained below, used to record an evoked response electrogram.

The channel interfaces include analog-to-digital converters for digitizing sensing signal inputs from the sensing amplifiers, registers that can be written to for adjusting the gain and threshold values of the sensing amplifiers, and, in the case of the ventricular and atrial channel interfaces, registers for controlling the output of pacing pulses and/or adjusting the pacing pulse energy by changing the pulse amplitude or pulse width. The microprocessor 1610 controls the overall operation of the device in accordance with programmed instructions stored in memory. The sensing circuitry of the defibrillator 1600 generates atrial and ventricular sense signals when voltages sensed by the electrodes exceed a specified threshold. The controller then interprets sense signals from the sensing channels and controls the delivery of paces in accordance with a programmed pacing mode. The sensed signals from any of the sensing channels of the defibrillator 1600 in FIG. 5 can be digitized and recorded by the controller to constitute an electrogram that can either be transmitted via the telemetry link 1680 to the external programmer 1675 or stored for later transmission. The patient's cardiac activity may thus be observed in real-time or over a selected historical period.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as "arranged", "arranged and configured", "constructed and arranged", "constructed", "manufactured and arranged", and the like.

All publications and patent applications in this specification are indicative of the level of ordinary skill in the art to which the present technology pertains. All publications and patent applications are herein incorporated by reference to the same extent as if each individual publication or patent application was specifically and individually indicated by reference.

This application is intended to cover adaptations or variations of the present subject matter. It is to be understood that the above description is intended to be illustrative, and not restrictive.

We claim:

1. A shock deferral unit comprising:

a bi-directional communication device configured to receive a notification of an impending shock from a defibrillator and configured to send an instruction to defer the impending shock to the defibrillator;

an authentication interface configured to receive authentication data from a user;

a user instruction interface configured to receive the instruction to defer the impending shock from the user; and an authentication device configured to authenticate the user based on the authentication data and instruct the bi-directional communication device to send the instruction to defer a shock upon authentication and receipt of the instruction to defer the shock, wherein the shock deferral unit is portable by an ambulatory patient, and wherein the authentication interface is configured to receive authentication data from a user and the user instruction interface is configured to send the instruction to defer shock within a 60-second time period.

2. The shock deferral unit of claim 1, wherein the bi-directional communication device is a radio.

3. The shock deferral unit of claim 1, further comprising a user interface configured to display the notification of the impending shock.

4. The shock deferral unit of claim 3, wherein the bi-directional communication device is configured to relay one or more physiological measurements sensed by the defibrillator to the user interface.

5. The shock deferral unit of claim 1, wherein the shock deferral unit is configured to be at least one in the group consisting of: wearable by, manually holdable by, and pocketable by a patient.

6. The shock deferral unit of claim 1, wherein the authentication interface is configured to receive at least one type of authentication data from the user in the group consisting of: textual, verbal, haptic, and biometric data.

7. A shock deferral system comprising:

a defibrillator configured to sense patient physiological measures, communicate a notification of impending shock, and deliver shock therapy; and a bi-directional communication device configured to receive a notification of impending shock from the defibrillator and configured to send an instruction to defer the impending shock to the defibrillator;

an authentication interface configured to receive authentication data from a user;

a user instruction interface configured to receive the instruction to defer the impending shock from the user; and an authentication device configured to receive the authentication data from the authentication interface, and authenticate the user based on the authentication data;

wherein the defibrillator is configured to defer shock upon authentication by the authentication device and receipt of the instruction to defer the shock, wherein the authentication interface and the user instruction interface are portable by an ambulatory patient, and wherein the authentication interface is configured to receive authentication data from a user and the user instruction interface is configured to send the instruction to defer shock within a 60-second time period.

8. The shock deferral system of claim 7, wherein the defibrillator comprises the authentication device.

9. The shock deferral system of claim 7, wherein the authentication device is configured to authenticate the user each time the shock deferral unit receives a notification of impending shock from the defibrillator.

10. The shock deferral system of claim 7, wherein the bi-directional communication device is configured to relay one or more physiological measurements sensed by the defibrillator to a user interface.

11. A method comprising:

relaying a notification of impending shock therapy from a defibrillator to a user interface, wherein the user interface is portable by an ambulatory patient;

receiving authentication data from a user through an authentication interface in response to relaying the notification;

authenticating the user with the received authentication data;

receiving an instruction from the user to defer the impending shock therapy through a user input device; and sending the received instruction to the defibrillator to defer the impending shock therapy upon authentication, wherein receiving authentication data from a user occurs within 60 seconds of relaying the notification of impending shock.

12. The method of claim 11, wherein the authentication interface is at least one in the group consisting of: a biometric sensor, a microphone, and a manual user data entry device.

13. The method of claim 11 further comprising relaying a notification of at least one of: physiological measurements sensed by the defibrillator and shock deferral status to the user interface.

14. The method of claim 11 wherein the instruction from the user is received through at least one of: a watch, a pendant, a bracelet, eyeglasses, headphones, a mobile phone, a pen, a card, a box, and an adhesive accessory.

15. The method of claim 11 wherein sending the received instruction to the defibrillator is through radio frequency.

16. The method of claim 11 further comprising entering a training mode comprising soliciting a user for authentication data absent a notification of impending shock therapy.

* * * * *